United States Patent [19]

Zink

[11] Patent Number: 4,806,657

[45] Date of Patent: Feb. 21, 1989

[54] PROCESS FOR THE PREPARATION OF FLUORAN COMPOUNDS WHICH ARE SUBSTITUTED BY BASIC GROUPS

[75] Inventor: Rudolf Zink, Therwil, Switzerland

[73] Assignee: Ciba-Geigy Corporation, Ardsley, N.Y.

[21] Appl. No.: 860,706

[22] Filed: May 5, 1986

Related U.S. Application Data

[63] Continuation of Ser. No. 651,389, Sep. 17, 1984, abandoned.

[30] Foreign Application Priority Data

Sep. 26, 1983 [CH] Switzerland ............... 5199/83

[51] Int. Cl.$^4$ ..................................... C07D 311/88
[52] U.S. Cl. .................................................. 549/226
[58] Field of Search .......................................... 549/226

[56] References Cited

U.S. PATENT DOCUMENTS

| | | | |
|---|---|---|---|
| 3,669,711 | 6/1972 | Kimura et al. ............... | 549/226 |
| 3,681,390 | 8/1972 | Lin . | |
| 3,746,562 | 7/1973 | Lin . | |
| 3,873,573 | 3/1975 | Farber et al. ............... | 549/226 |
| 4,341,403 | 7/1982 | Igarashi et al. ............... | 549/226 |
| 4,414,399 | 11/1983 | Schmidt et al. ............... | 549/226 |

FOREIGN PATENT DOCUMENTS

| | | |
|---|---|---|
| 1306263 | 2/1973 | United Kingdom . |
| 1357244 | 6/1974 | United Kingdom . |

OTHER PUBLICATIONS

J. F. W. McOmie, Protective Groups in Organic Chemistry (1973), pp. 46-49.

Primary Examiner—Glennon H. Hollrah
Assistant Examiner—Mark W. Russell
Attorney, Agent, or Firm—Kevin T. Mansfield; Edward M. Roberts

[57] ABSTRACT

A process for the preparation of fluoran compounds which are substituted by basic groups and have the formula

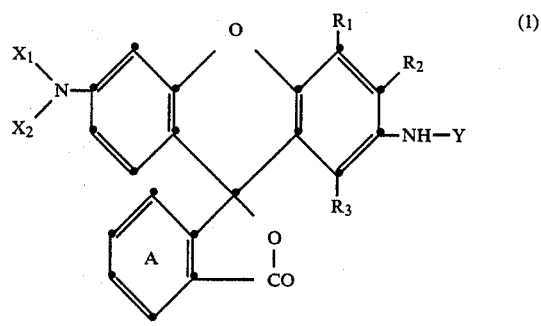

wherein
$R_1$, $R_2$ and $R_3$ are each independently hydrogen, halogen or lower alkyl, or $R_1$ and $R_2$ together with the carbon atom to which they are attached are a fused benzene nucleus,
$X_1$ and $X_2$ are each independently hydrogen, unsubstituted or substituted alkyl, cycloalkyl, aryl or aralkyl, or
$X_1$ and $X_2$ together with the nitrogen atom to which they are attached are a 5- or 6-membered heterocyclic radical, and
Y is unsubstituted or substituted alkyl, cycloalkyl, aryl or aralkyl, and
the ring A is unsubstituted or substituted, which process comprises reacting a ketonic acid of the formula

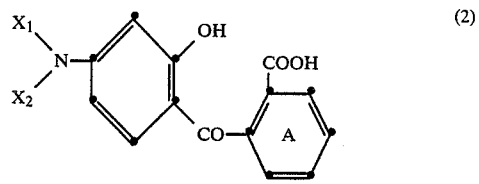

with a substituted 4-formylaminophenol derivative of the formula

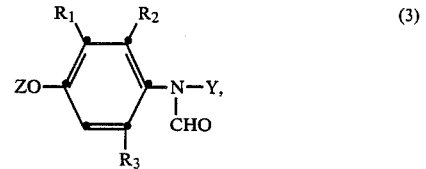

wherein A, $R_1$, $R_2$, $R_3$, $X_1$, $X_2$ and Y have the meanings assigned to them and Z is hydrogen, lower alkyl, formyl or lower alkanoyl, deformylating the resultant phthalide of the formula

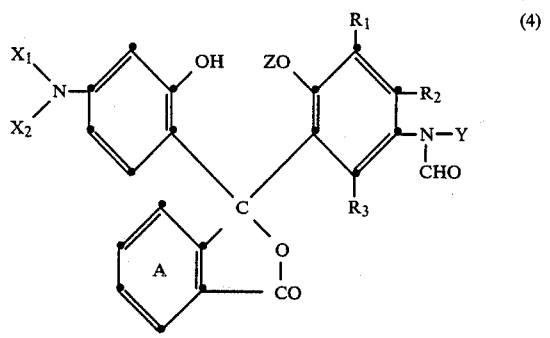

and cyclising the deformylated compound by intramolecular condensation to give the fluoran of the formula (1).

14 Claims, No Drawings

PROCESS FOR THE PREPARATION OF FLUORAN COMPOUNDS WHICH ARE SUBSTITUTED BY BASIC GROUPS

This application is a continuation of application Ser. No. 651,389, filed 9/17/84 now abandoned.

The present invention relates to a novel process for the preparation of fluoran compounds which are substituted by basic groups, in particular of 2,6-diaminofluorans which contain in the 2-position an amino group which is monosubstituted by an aliphatic, cycloaliphatic or araliphatic radical or, preferably, by an aromatic radical.

It is known from DE-OS 2 202 315 to prepare 2,6-diaminofluorans having a monophenylamino group in the 2-position by reacting an etherified 4-acetylaminophenol with a halobenzene to given an N-acetylated diphenylamine derivative, deacetylating said derivative, and condensing the diphenylamine so obtained with 2-(4'-dialkylamino-2'-hydroxybenzoyl)benzoic acid to give the fluoran compound. Further, the condensation of a 4-acetylanilino or 4-benzoylanilino compound, each of which may be further N-substituted, with 2-(4'-dialkylamino-2'-hydroxybenzoyl)benzoic acid to give the 2-N-acetylanilinofluoran or 2-N-benzoylanilinofluoran compound, with subsequent removal of the N-acetyl or N-benzoyl group, is taught in DE-OS 2 024 859.

Surprisingly, it has now been found that the reaction times can be shortened, the preparatory process simplified, and the yield of 2,6-diaminofluorans improved, by starting from the 4-formylaminophenol compound and carrying out the deformylation after the formation of the phthalide and before the formation of the fluoran.

Accordingly, the present invention provides a process for the preparation of fluoran compounds which are substituted by basic groups and have the formula

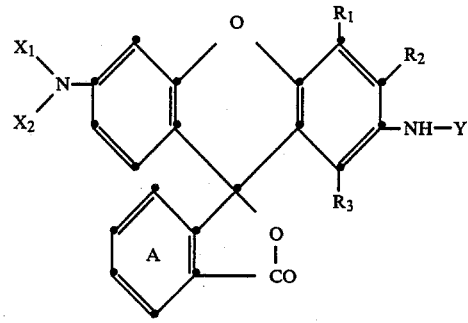

wherein
$R_1$, $R_2$ and $R_3$ are each independently hydrogen, halogen or lower alkyl, or $R_1$ and $R_2$, together with the carbon atom to which they are attached, are a fused benzene nucleus,
$X_1$ and $X_2$ are each independently hydrogen, alkyl containing not more than 12 carbon atoms which is unsubstituted or substituted by halogen, hydroxy, cyano or lower alkoxy, or are cycloalkyl, aryl or aralkyl; or $X_1$ and $X_2$, together with the nitrogen atom to which they are attached, are a 5- or 6-membered, preferably saturated heterocyclic radical, and
Y is alkyl containing not more than 12 carbon atoms which is unsubstituted or substituted by halogen, hydroxy, cyano or lower alkoxy, or is cycloalkyl, aryl or aralkyl, and
the ring A is unsubstituted or substituted by nitro, amino, mono-lower alkylamino, di-lower alkylamino or halogen.

The process comprises reacting a ketonic acid of the formula

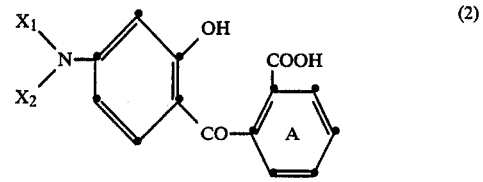

with a substituted 4-formylaminophenol derivative of the formula

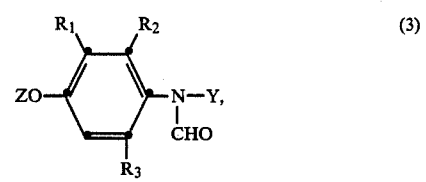

wherein A, $R_1$, $R_2$, $R_3$, $X_1$, $X_2$ and Y have the given meanings and Z is hydrogen, lower alkyl, formyl or lower alkanoyl, deformylating the resultant phthalide of the formula

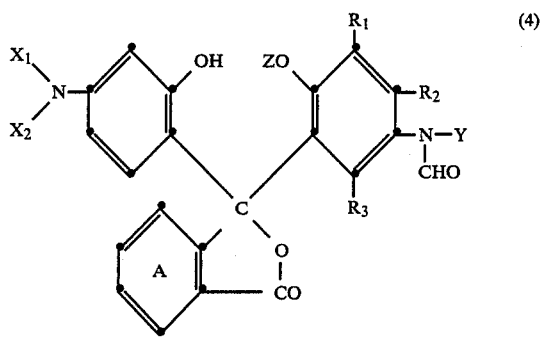

and cyclising the deformylated phthalide by intramolecular condensation to give the fluoran of the formula (1).

Z is preferably hydrogen, methyl, ethyl, formyl or acetyl. Most preferably, Z is hydrogen or, in particular, methyl.

In the definition of the radicals of the fluorans, lower alkyl and lower alkoxy usually denote those groups or moieties which contain from 1 to 5, preferably from 1 to 3, carbon atoms. Lower alkyl groups are for example methyl, ethyl, n-propyl, isopropyl, n-butyl, sec-butyl, tert-butyl, amyl or isoamyl; and lower alkoxy groups are for example methoxy, ethoxy, isopropoxy or tert-butoxy.

Alkyl groups represented by $X_1$, $X_2$ and Y may be in a straight chain or branched chain configuration and are for example: methyl, ethyl, n-propyl, isopropyl, n-butyl, sec-butyl, amyl, isoamyl, n-hexyl, 2-ethylhexyl, n-heptyl, n-octyl, isooctyl, n-nonyl, isononyl or n-dodecyl.

Substituted alkyl groups $X_1$, $X_2$ and Y are preferably cyanoalkyl, haloalkyl, hydroxyalkyl or alkoxyalkyl, each preferably containing in all 2 to 4 carbon atoms. Examples of such groups are: β-cyanoethyl, β-chloroethyl, γ-chloropropyl, β-hydroxyethyl, γ-hydroxypropyl, β-methoxyethyl or β-ethoxyethyl.

Cycloalkyl represented by $X_1$, $X_2$ and Y is for example cyclopentyl, cycloheptyl, or, preferably, cyclohexyl. The cycloalkyl radicals may contain one or more $C_1$–$C_4$alkyl radicals, in particular methyl groups, and preferably have in all 5 to 10 carbon atoms.

Aralkyl represented by $X_1$, $X_2$ and Y is normally phenylethyl or, preferably, benzyl; whereas aryl is preferably naphthyl, diphenyl or, most preferably, phenyl. The aralkyl and aryl radicals may be substituted by halogen, trifluoromethyl, cyano, nitro, lower alkyl, lower alkoxy, lower alkoxycarbonyl or lower alkylcarbonyl.

Preferred substitutents in the benzyl and phenyl moieties of the radicals $X_1$, $X_2$ and Y are for example halogen, trifluoromethyl, cyano, methyl, methoxy or carbomethoxy. Examples of such araliphatic and aromatic radicals are methylbenzyl, chlorobenzyl, cyanophenyl, tolyl, xylyl, chlorophenyl, trifluoromethylphenyl, methoxyphenyl or carbomethoxyphenyl.

A heterocyclic radical —$NX_1X_2$ is for example pyrrolidino, piperidino, pipecolino, morpholino, thiomorpholino or piperazino, e.g. methylpiperazino. Preferred saturated heterocyclic radicals —$NX_1X_2$ are pyrrolidino, piperidino or morpholino.

The substitutents $X_1$ and $X_2$ can be identical or different. $X_1$ is preferably $C_1$–$C_8$alkyl, cyclohexyl, phenyl, tolyl, benzyl or, most preferably, lower alkyl. $X_2$ is preferably lower alkyl or benzyl and, most preferably, methyl or ethyl.

The further N-substitutent Y is preferably $C_1$–$C_8$alkyl, benzyl, cyclohexyl or, most preferably, phenyl which is unsubstituted or substituted by methyl, halogen, trifluoromethyl or carbomethoxy. A particularly preferred N-substituent Y is n-octyl, benzyl, xylyl, chlorophenyl, tolyl, trifluoromethylphenyl and, most preferably, phenyl. The preferred xylyl radical is 2,4-dimethylphenyl.

$R_1$, $R_2$ and $R_3$ are preferably hydrogen, halogen or methyl.

The ring A is preferably not further substituted. If it does contain substituents, then these are preferably halogen, nitro or di-lower alkylamino.

Halogen is for example fluorine, bromine, iodine or, preferably, chlorine.

The reactants are preferably employed in molar amounts when carrying out the process of this invention.

The process of the present invention for preparing fluorans of the formula (1) which are substituted by basic groups is conveniently carried out in three steps in which the intermediates obtained can be further used without isolation.

The first step, in which the ketonic acid of the formula (2) is reacted with the substituted 4-formylaminophenol derivative of the formula (3), is suitably carried out in concentrated sulfuric acid (e.g. having a concentration of 50–100%, preferably 90–98%) in the temperature range from 0° to 60° C., preferably from 5° to 40° C. The reaction time depends on the temperature and on the starting materials and is generally from ½ hour to 10 hours, preferably from 1 to 5 hours.

Upon completion of the first step, the reaction product of the formula (4) can be further used direct for the removal of the formyl group. If it is desired to isolate the intermediate, the sulfuric acid containing solution of the reaction product is poured into a copious amount of ice-water to precipitate the product, which is collected by filtration.

The second reaction step, i.e. the deformylation of the phthalide of the formula (4), is preferably carried out by either first diluting the sulfuric acid containing solution obtained in the first step with water, or by dissolving the isolated intermediate of the formula (4) in dilute sulfuric acid and then heating the dilute acid solutions to 80° to 100° C.

The reaction time of the second step is generally from 15 to 90 minutes, preferably from 20 to 60 minutes.

The hot solutions are then conventionally poured into ice-water and the precipitated deformylated phthalide compound is isolated.

To obtain the desired final product, the phthalide compound is advantageously dissolved or dispersed in a polar solvent and treated with a base, preferably in the temperature range from 40° to 100° C.

The reaction time of the third step is usually from 10 to 90 minutes, preferably from 20 to 60 minutes.

Suitable polar solvents are water or water-miscible organic solvents, e.g. aliphatic $C_1$–$C_4$ alcohols such as methanol, ethanol, propanol, isopropanol or isobutanol; alkylene glycols such as ethylene glycol or propylene glycol; monoalkyl glycol ethers such as ethylene glycol monomethyl, monoethyl or monobutyl ether, and diethylene glycol monomethyl or monoethyl ether; ketones such as acetone, methyl ethyl ketone, cyclohexanone, diacetone alcohol; ethers and acetals, e.g. diisopropyl ether, diphenyl oxide, dioxan, tetrahydrofuran, and also tetrahydrofurfuryl alcohol, pyridine, acetonitrile, γ-butyrolactone, N,N-dimethylformamide, N,N-dimethylacetamide, tetramethylurea, tetramethylenesulfone, and others. Mixtures of these solvents can also be used. Water and ethanol are preferred.

Suitable bases are alkali metal hydroxides, e.g. sodium or potassium hydroxide, ammonia, alkali metal carbonates or bicarbonates, ammonium carbonate or ammonium bicarbonate, dialkyl- or trialkylamines or dialkanol- or trialkanolamines; and mixtures thereof. The most preferred base is potassium carbonate.

The final product of the formula (1) is isolated in generally known manner by separating the precipitate and washing and drying the filter cake, or by treating it with a suitable organic solvent, e.g. methanol, ethanol or isopropanol, and, if necessary, recrystallising the product, e.g. from toluene.

A particularly suitable embodiment of the novel process comprises condensing the ketonic acid of the formula (2) and the 4-formylaminophenol derivative of the formula (3) in concentrated sulfuric acid in the temperature range from 10° to 40° C., preferably for 1 to 3 hours, diluting the sulfuric acid containing solution of the phthalide compound of the formula (4) with water, and heating the dilute solution to 80° to 100° C., preferably for 20° to 60° C. The deformylated phthalide compound is then isolated and treated in an aqueous-alcoholic solution with a base, e.g., triethylamine or, preferably, potassium carbonate, at 60° to 90° C., and then isolating the fluoran of the formula (1).

Examples of ketonic acids of the formula (2) employed as starting materials are:
2-(4′-dimethylamino-2′-hydroxybenzoyl)benzoic acid,
2-(4′-diethylamino-2′-hydroxybenzoyl)benzoic acid,
2-(4′-di-n-butylamino-2′-hydroxybenzoyl)benzoic acid, 2-(4'-N-methyl-N-cyclohexylamino-2'-hydroxybenzoyl)benzoic acid,
2-(4'-N-phenyl-N-methylamino-2'-hydroxybenzoyl)benzoic acid,
2-(4'-N-o-, m- or p-tolyl-N-methylamino-2'-hydroxybenzoyl)benzoic acid,
2-(4'-N-o-, m- or p-tolyl-N-ethylamino-2'-hydroxybenzoyl)benzoic acid,
2-(4'-N-pyrrolidino-2'-hydroxybenzoyl)benzoic acid,
2-(4'-N-piperidino-2'-hydroxybenzoyl)benzoic acid,
2-(4'-N-methyl-N-n-amylamino-2'-hydroxybenzoyl)benzoic acid,
2-(4'-N-ethyl-N-isoamylamino-2'-hydroxybenzoyl)benzoic acid,
2-(4'-dibenzylamino-2'-hydroxybenzoyl)benzoic acid.

Representative examples of 4-N-formylaminophenol derivatives of the formula (3) are:
4-N-formyl-N-ethylaminophenol,
4-N-formyl-N-octylaminophenol,
4-N-formyl-N-n-octylamino-1-methoxybenzene
4-N-formyl-N-benzylamino-1-methoxybenzene,
4-N-formyl-N-phenylamino-1-methoxybenzene,
4-N-formyl-N-2'-chlorophenylamino-1-methoxybenzene,
4-N-formyl-N-4'-chlorophenylamino-1-methoxybenzene,
4-N-formyl-N-3'-trifluoromethylphenylamino-1-methoxybenzene,
4-N-formyl-N-4'-trifluoromethylphenylamino-1-methoxybenzene,
4-N-formyl-N-o-, m- or p-tolylamino-1-methoxybenzene,
4-N-formyl-N-xylylamino-1-methoxybenzene,
4-N-formyl-N-phenylamino-1-methoxy-2-methylbenzene,
4-N-formyl-N-phenylamino-1-methoxy-2-chlorobenzene,
4-N-formyl-N-phenylamino-1-methoxy-3-methylbenzene (N-formyl-4-methoxy-2-methyldiphenylamine)
4-N-formyl-N-phenylamino-1-methoxy-3-chlorobenzene,
4-N-formyl-N-3'-trifluoromethyl-phenylamino-1-methoxy-3-methylbenzene,
4-N-formyl-N-cyclohexylamino-1-methoxybenzene or
4-N-formyl-2',4'-dimethylanilino-1-methoxy-3-methylbenzene.

The starting materials of the formula (3) can be prepared by reacting, for example, a 4-formylaminophenol derivative of the formula

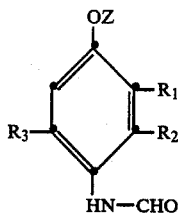

(5)

with a halogen compound of the formula Y-Hal, wherein Hal is iodine, chlorine, fluorine or, preferably, bromine, and $R_1$, $R_2$, $R_3$, and Y and Z have the meanings assigned to them.

The introduction of the substituent Y into the formylamino group is effected in general by known procedures. It is preferred to carry out the reaction in the presence of an acid acceptor and, if appropriate, in the presence of a copper catalyst. The acid acceptor can be any basic compound. It is preferred to use a tertiary organic base as acid acceptor, for example quinoline, pyridine, a substituted pyridine, triethylamine or triethanolamine or, in particular, a basic inorganic salt, for example an alkali metal carbonate or bicarbonate, e.g. sodium carbonate, potassium carbonate or sodium bicarbonate, ammonium bicarbonate, or an alkali metal phosphate or borate, e.g. disodium hydrogen phosphate or sodium hydrogen borate, and mixtures thereof with the above-mentioned organic bases.

The copper catalyst can be metallic copper or any copper(I) or copper(II) compound. The preferred catalyst is metallic copper. Examples of eligible copper catalysts are: copper(I) chloride, copper(I) bromide, copper(I) iodide or copper(I) cyanide, and, principally, copper powder.

When using halogen compounds of the formula Y-Hal, in which Y is an aryl radical, it is preferred to carry out the reaction by adding small amounts of copper powder and iodine.

The preferred fluoran compounds which are substituted by basic groups and prepared by the process of this invention are those of the formula (1), wherein each of $R_1$, $R_2$ and $R_3$ independently is hydrogen, chlorine or methyl, each of $X_1$ and $X_2$ independently is $C_1$–$C_8$alkyl, cyclohexyl, tolyl or benzyl or —$NX_1X_2$ is pyrrolidino or piperidino, Y is $C_1$–$C_8$alkyl, phenyl, chlorophenyl, trifluoromethylphenyl, tolyl, xylyl or benzyl, and the ring A is unsubstituted. The most preferred fluoran compounds of the formula (1) are those wherein $R_1$ and $R_3$ are hydrogen, $R_2$ is hydrogen or methyl, and each of $X_1$ and $X_2$ is lower alkyl or cyclohexyl, or —$NX_1X_2$ is pyrrolidino and Y is phenyl, tolyl, chlorophenyl, xylyl or trifluoromethylphenyl.

A considerable advantage of the present invention resides in the feature that it is easy to carry out technically and affords pure final products in very good yield without isolation of the N-formylphthalide compound obtained as intermediate. Compared with the closest procedure known from the prior art, it is possible to obtain a more than threefold improvement in yield by the step of deformylating the phthalide compound formed as intermediate.

The fluoran compounds of the formula (1) prepared by the process of this invention are normally colourless or at most faintly coloured. They are particularly suitable rapidly developing colour formers for use in a heat-sensitive or, preferably, in a pressure-sensitive recording material which can also be a copying material. When these colour formers are brought into contact preferably with an acid developer, i.e. an electron acceptor, they produce on clays and phenolic substrates strong green, grey or black colorations which are fast to sublimation and light.

The invention is illustrated by the following Examples in which percentages are by weight, unless otherwise stated.

EXAMPLE 1

15.65 g of 4-diethylamino-2-hydroxybenzophenone-2'-carboxylic acid (ketonic acid) are dissolved at 45° C. in 75 g of 98% sulfuric acid. The solution is cooled to 5° C. and 12 g of N-formyl-4-methoxy-2-methyldiphenylamine are added over 1 hour at a maximum temperature of 10° C. The temperature is allowed to rise to 25° C. and kept for 2 hours. The resultant solution is poured into ice-water and the product precipitates. The precipitate is isolated by filtration and neutralised by suspending it in dilute ammonia. The product is again isolated by filtration and washed and dried, affording 26.8 g of the phthalide compound of the formula

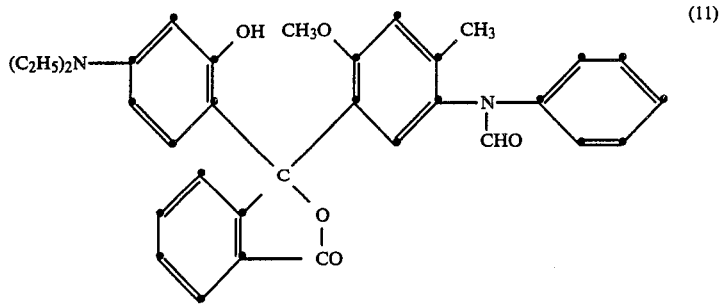
(11)

with a melting point of 173°–174° C. (dec.).

| Elemental analysis | C | H | N |
|---|---|---|---|
| % calculated | 73.9 | 6.0 | 5.2 |
| % found | 73.9 | 6.1 | 5.1 |

26.8 g of the phthalide compound of the formula (11) are charged into 140 g of 50% sulfuric acid and the mixture is heated to 90°–100° C. This temperature is kept for ½ hour and the resultant solution is poured into ice-water, whereupon the product precipitates and is isolated by filtration. The precipitate is neutralised in dilute ammonia at 25° C., isolated by filtration once more and dried, affording 25.4 g of the phthalide compound of the formula

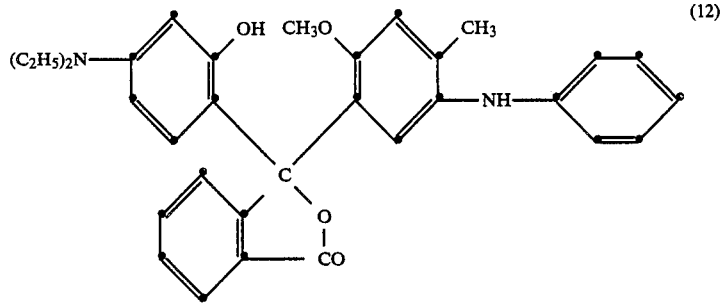
(12)

with a melting point of 180°–181° C.

| Elemental analysis | C | H | N |
|---|---|---|---|
| % calculated | 75.6 | 6.3 | 5.5 |
| % found | 75.7 | 6.3 | 5.5 |

25.4 g of the phthalide compound of the formula (12) are dissolved at 70° C. in 75 ml of 94% ethanol. To this solution are added 25 ml of water and 3.5 g of potassium carbonate. The mixture is stirred for 1 hour at 75°–80° C. and the product precipitates. Then 40 ml of water are added and the batch is cooled to 10° C. The crystalline precipitate is isolated by filtration, washed with ethanol and water and dried. Yield: 20.7 g of the fluoran compound of the formula

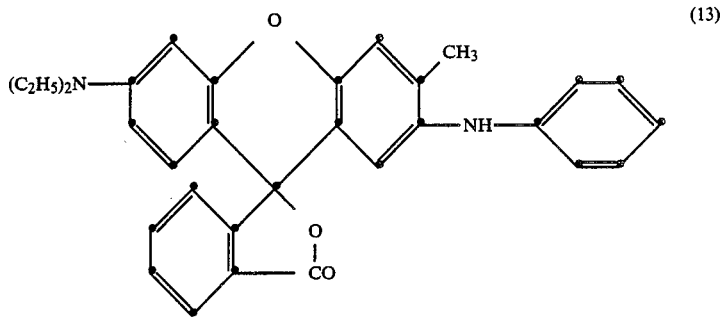
(13)

which melts at 189°–190° C. The yield is 83.5% of theory, based on the N-formyl-4-methoxy-2-methyldiphenylamine.

The N-formyl-4-methoxy-2-methyldiphenylamine used for the above reaction with the ketonic acid can be prepared as follows:

137 g of 2-amino-5-methoxytoluene are formylated by boiling for 1 hour in 85% formic acid at 100° C. 165 g of the N-formylated compound so obtained of the formula

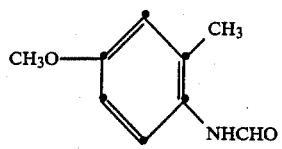

(m.p. 103°–104° C.) are dissolved at 110° C. in 108 g of bromobenzene and to the solution are added, in succession, 75 g of potassium carbonate, 2 g of copper powder and 2 g of iodine. The temperature is gradually raised over 6 hours until it has reached 172° C. With stirring and under a stream of nitrogen, the water of reaction and excess bromobenzene are distilled off over the course of 15 to 40 hours. Fractional distillation (b.p.=0.03/155°–159° C.) yields 142 g of N-formyl-4-methoxy-2-methyldiphenylamine.

The following 2,6-diaminofluorans of the formula (15) listed in the table are prepared in similar manner using the appropriate ketonic acids and N-formyl-4-methoxyanilines.

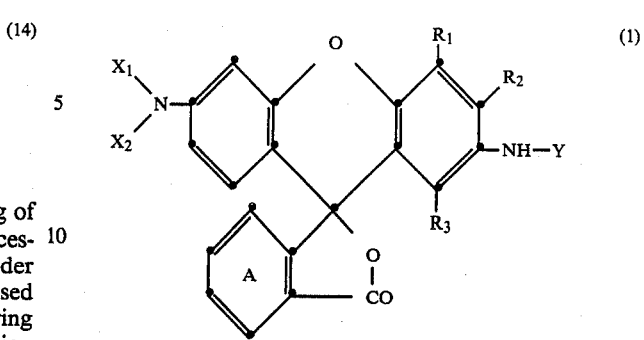

wherein

R$_1$, R$_2$ and R$_3$ are each independently hydrogen, halogen or lower alkyl, or R$_1$ and R$_2$, together with the carbon atoms to which they are attached, form a fused benzene nucleus, X$_1$ and X$_2$ are each independently hydrogen, alkyl containing not more than 12 carbon atoms which is unsubstituted or substituted by halogen, hydroxy, cyano or lower alkoxy, or are cycloalkyl, aryl or aralkyl; or X$_1$ and X$_2$, together with the nitrogen atom to which they are attached, form a 5- or 6-membered heterocyclic ring selected from pyrrolidino, piperidino, pipecolino, morpholino, thiomorpholino, piperazino and methylpiperazino, and

TABLE

| Example | $-N\begin{smallmatrix}X_3\\X_4\end{smallmatrix}$ | R' | Y' | m.p./°C. | *Yield in % |
|---|---|---|---|---|---|
| 2 | —N(C$_2$H$_5$)$_2$ | H | n-C$_8$H$_{17}$ | 123–125 | 71.5 |
| 3 | —N(C$_2$H$_5$)$_2$ | CH$_3$ | 2,5-dimethylphenyl | 156–158 | 71.4 |
| 4 | —N(CH$_3$)(cyclohexyl) | CH$_3$ | phenyl | 188–191 | 56.6 |
| 5 | —N(pyrrolidino) | CH$_3$ | phenyl | 220–221 | 74.7 |

*The yield is based on the corresponding N—formyl-4-methoxyaniline.

What is claimed is:

1. A process for the preparation of a fluoran which is substituted by basic groups and has the formula Y is alkyl containing not more than 12 carbon atoms which is unsubstituted or substituted by halogen, hydroxy, cyano or lower alkoxy, or is cycloalkyl, aryl or aralkyl, and the ring A is unsubstituted or substituted by nitro, amino, mono-lower alkylamino, di-lower alkylamino or halogen, which process comprises (1), reacting a ketonic acid of the formula

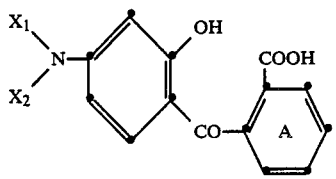

(2)

with a substituted 4-formylaminophenol derivative of the formula

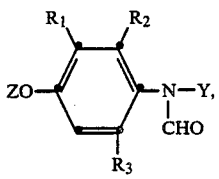

(3)

wherein A, $R_1$, $R_2$, $R_3$, $X_1$, $X_2$ and Y have the meanings assigned to them and Z is hydrogen, lower alkyl, formyl or lower alkanoyl, (2), deformylating the resultant phthalide of the formula

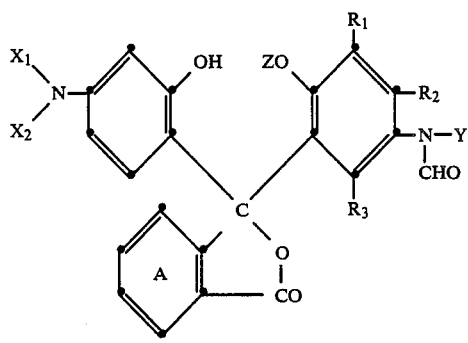

(4)

by heating in dilute sulfuric acid at 80° to 100° C. for 15 to 90 minutes and (3), cyclising the deformylated phthalide by intramolecular condensation to give the fluoran of the formula (1).

2. A process according to claim 1, wherein $X_1$ is $C_1$-$C_8$alkyl, cyclohexyl, phenyl, tolyl or benzyl, and $X_2$ is lower alkyl or benzyl, or —$NX_1X_2$ is pyrrolidino or piperidino.

3. A process according to claim 1, wherein Y is $C_1$-$C_8$alkyl, benzyl, cyclohexyl, phenyl, or phenyl which is substituted by halogen, methyl, trifluoromethyl or carbomethoxy.

4. A process according to claim 1, wherein each of $R_1$, $R_2$ and $R_3$ independently is hydrogen, halogen or methyl.

5. A process according to claim 1, wherein the ring A is unsubstituted.

6. A process according to claim 1, wherein each of $R_1$, $R_2$ and $R_3$ independently is hydrogen, chlorine or methyl, $X_1$ and $X_2$ are $C_1$-$C_8$alkyl, cyclohexyl, tolyl or benzyl, or —$NX_1X_2$ is pyrrolidino or piperidino, Y is $C_1$-$C_8$alkyl, benzyl, phenyl, chlorophenyl, tolyl, xylyl or trifluoromethylphenyl, and the ring A is unsubstituted.

7. A process according to claim 6, wherein $R_1$ and $R_3$ are hydrogen, $R_2$ is hydrogen or methyl, $X_1$ and $X_2$ are lower alkyl or cyclohexyl, or —$NX_1X_2$ is pyrrolidino and Y is phenyl, tolyl, xylyl, chlorophenyl or trifluoromethylphenyl.

8. A process according to claim 1, wherein Z is hydrogen, methyl, ethyl, formyl or acetyl.

9. A process according to claim 8, wherein Z is hydrogen or methyl.

10. A process according to claim 1, wherein the condensation of the ketonic acid of the formula (2) is carried out with the 4-formylaminophenol derivative of the formula (3) in concentrated sulfuric acid at 0° to 50° C.

11. A process according to claim 1, which comprises heating a dilute sulfuric acid containing solution of the phthalide compound of the formula (4) at 80° to 100° C. for 20 to 60 minutes.

12. A process according to claim 1, which comprises dissolving or dispersing the deformylated phthalide compound in a polar solvent, and treating the solution or dispersion so obtained with a base in the temperature range from 40° to 100° C.

13. A process according to claim 1, which comprises condensing the ketonic acid of the formula (2) and the 4-formylaminophenol derivative of the formula (3) in concentrated sulfuric acid at 10° to 40° C., diluting the sulfuric acid containing solution of the reaction product of the formula (4) with water and heating it at 80° to 100° C. for 15 to 90 minutes, isolating the deformylated phthalide compound and treating it with a base at 60° to 90° C.

14. A process according to claim 1, wherein $R_1$ and $R_3$ are hydrogen, $R_2$ is hydrogen or methyl, $X_1$ is methyl, ethyl or cyclohexyl, $X_2$ is methyl or ethyl, or —$NX_1X_2$ is pyrrolidino, Y is n-octyl, phenyl or xylyl, and the ring A is unsubstituted.

* * * * *